United States Patent [19]

Commons et al.

[11] Patent Number: 5,169,844
[45] Date of Patent: Dec. 8, 1992

[54] 4-SUBSTITUTED PIPERIDINECARBOXYLIC ACID ESTERS: INHIBITION OF CHOLESTEROL ABSORPTION

[75] Inventors: Thomas J. Commons, Chester; Donald P. Strike, Delaware, both of Pa.

[73] Assignee: American Home Products Corporation, New York, N.Y.

[21] Appl. No.: 812,512

[22] Filed: Dec. 20, 1991

[51] Int. Cl.$^5$ .......................................... A61K 31/445
[52] U.S. Cl. .................................... 514/211; 514/212; 514/227.8; 514/237.2; 514/316; 514/327; 540/488; 540/524; 544/58.4; 544/129; 546/188; 546/216
[58] Field of Search ................. 514/237.2, 327, 227.8, 514/316, 424, 211, 212; 546/188, 216; 544/58.4, 129; 540/488, 524

[56] References Cited

U.S. PATENT DOCUMENTS 3,322,818  5/1967  Hanze .................... 544/58.4
4,060,609  11/1977 Schacht et al. ............ 514/316
4,139,620  2/1979  Boswell ................. 514/237.2

FOREIGN PATENT DOCUMENTS 2612186  9/1988  France .
0045107  3/1982  Japan ..................... 514/212

OTHER PUBLICATIONS

Bhat et al., Biochem. Biophys. Res. Commun. 109, 486 (1982).
Gallo et al., J. Lipid Research, 25, 604 (1984).
Hosie et al., J. Biol. Chem. 262, 260 (1987).
Stout et al., Biochem. Biophys. Acta, 837, 6 (1985).
Field, J. Lipid Research, 25, 389 (1984).
Cayen et al., J. Lipid Research, 20, 162 (1979).
Foldes et al., J. Pharmacol. Exptl. Therap. 122, 457–464 (1958).
Sumida et al., Plant & Call Physiol. 14, 781–785 (1973).
van den Berg et al., Pestic. Sci. 13, 19–38 (1982).
Derwent Abstract 81-55962-D of Japanese Patent J56071-058.

Primary Examiner—Donald G. Daus
Attorney, Agent, or Firm—Robert F. Boswell, Jr.

[57] ABSTRACT

Inhibition of the enzymes cholesterol ester hydrolase (CEH) and/or acyl coenzyme A: cholesterol acyltransferase (ACAT) results in inhibition of absorption of cholesterol and thus lowers serum cholesterol levels. Compounds of the formula below:

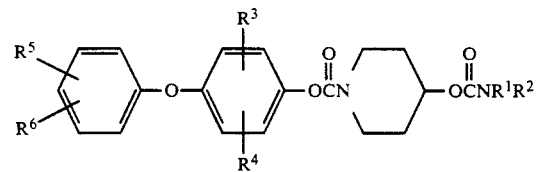

where $R^1$ is selected from alkyl, alkenyl, cycloalkyl, cycloalkylalkyl or arylalkyl and $R^2$ is hydrogen or alkyl or $-NR^1R^2$ is morpholine, thiomorpholine or 4-substituted or unsubstituted piperidine and $R^3$, $R^4$, $R^5$, $R^6$ are hydrogen, alkyl, alkoxy, halogen, nitro, cyano, perhaloalkyl, alkanoyloxy, alkoxycarbonyl or hydroxycarbonyl have been shown to inhibit the enzymes CEH and/or ACAT in in vitro tests to inhibit absorption of radio-labeled cholesterol in rats.

22 Claims, No Drawings

4-SUBSTITUTED PIPERIDINECARBOXYLIC ACID ESTERS: INHIBITION OF CHOLESTEROL ABSORPTION

BACKGROUND OF THE INVENTION

1. Field of Invention

This invention relates to novel 4-substituted piperidinecarboxylic acid esters which inhibit the absorption of cholesterol in rats and have been shown to inhibit the enzymes cholesterol ester hydrolase (CEH) and/or acyl coenzyme A: cholesterol acyltransferase (ACAT). Each of these enzymes is implicated in the reesterification and absorption of exogenous cholesterol. It has been shown that the removal of CEH from pancreatic juice results in an 80% reduction in the uptake of cholesterol (Gallo et al, Journal of Lipid Research 25, 604–612 (1984)). Reduction of high blood cholesterol levels is a concern of health conscious individuals. The association between high serum cholesterol levels and coronary heart disease is well documented, and consequently, compounds of this invention may be useful in the treatment of atherosclerosis, familial hypercholesterolemia, hyperlipemia, and like diseases.

2. Information Disclosure Statement

Hoisie, et al., J. Biol. Chem. 262, 260–264 (1987) has reported that p-nitrophenyl-N-alkylcarbamates and cholesteryl-N-alkylcarbamates inhibit the porcine pancreatic cholesterol esterase (CEH) hydrolysis of p-nitrophenylbutyrate, thus an indication that phenylcarbamates may have utility in decreasing blood cholesterol via inhibition of CEH and/or ACAT. Cholesterol ester hydrolase inhibition by 4-phenoxyphenyl esters of N-alkylcarbamic acids which includes the intermediate 4-phenoxyphenyl esters of 4-hydroxy-1-piperidinecarboxylic acid used as intermediates in the present invention is disclosed in our commonly owned U.S. Application Ser. No. 07/594,241 filed Oct. 9, 1990.

SUMMARY OF THE INVENTION

The novel cholesterol absorption inhibitors of this invention are substituted carbamic acid 1-[(4-phenoxyphenoxy)carbonyl]-4-piperidinyl esters having the formula:

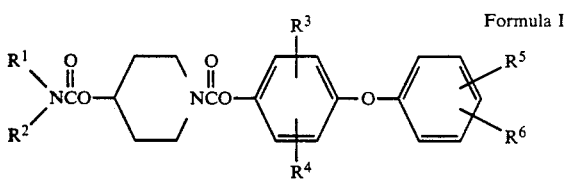

Formula I in which
R$^1$ is H, C$_1$–C$_{20}$ alkyl, C$_3$–C$_{20}$ alkenyl, C$_3$–C$_8$ cycloalkyl, cycloalkylalkyl where the cycloalkyl moiety has from 3 to 8 carbon atoms and the alkyl moiety has from 1 to 6 carbon atoms, phenyl, phenyl substituted by C$_1$–C$_6$ alkyl, C$_1$–C$_6$ alkoxy, halo, nitro, cyano or trifluoromethyl; phenylalkyl where the alkyl moiety has from 1 to 20 carbons, or phenylalkyl where the phenyl group is substituted by C$_1$–C$_6$ alkyl, C$_1$–C$_6$ alkoxy, halo, nitro, cyano, trifluoromethyl or phenyl; R$^2$ is H or C$_1$–C$_6$ alkyl; or R$^1$ and R$^2$ taken together with the interposed nitrogen forms a heterocyclic group of the formula:

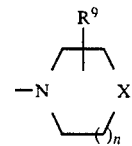

where n is one of the intergers 0, 1 or 2;
X is —O—, —S—, or

and
R$^7$ is H, hydroxy, C$_1$–C$_6$ alkyl, C$_2$–C$_6$ alkanoyloxy, C$_1$–C$_6$ hydroxyalkyl, carboxyl, C$_1$–C$_{16}$ alkoxycarbonyl, phenyl or phenyl substituted with C$_1$–C$_6$ alkyl, C$_1$–C$_6$ haloalkyl, C$_1$–C$_6$ perhaloalkyl, halo, nitro or cyano;
R$^8$ is H or C$_1$–C$_6$ alkyl or
R$^7$ and R$^8$ taken together with the intervening carbon atom forms a polymethylene ring of 3 to 7 carbon atoms;
R$^9$ is H, C$_1$–C$_6$ alkyl or C$_2$–C$_{12}$ gemdialkyl;
R$^3$, R$^4$, R$^5$ and R$^6$ are H, C$_1$–C$_6$ alkyl, C$_1$–C$_6$ alkoxy, halo, nitro, cyano, C$_1$–C$_6$ perhaloalkyl, C$_1$–C$_{16}$ alkoxycarbonyl, or carboxyl.

The preferred compounds of this invention, based upon their in vivo and in vitro cholesterol absorption inhibition properties, are those of the formula I:

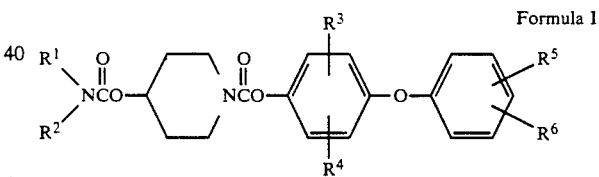

Formula I in which
R$^1$ is C$_1$–C$_{20}$ alkyl, C$_3$–C$_{20}$ alkenyl, C$_3$–C$_8$ cycloalkyl, cycloalkylalkyl in which the cycloalkyl moiety has from 3 to 8 carbon atoms and the alkyl moiety has from 1 to 6 carbon atoms, phenylalkyl where the alkyl moiety has from 1 to 20 carbon atoms, and substituted phenylalkyl where the phenyl group is substituted by C$_1$–C$_6$ alkyl, C$_1$–C$_6$ alkoxy, halo, nitro, cyano, trifluoromethyl, or phenyl;
R$^2$ is H or C$_1$–C$_6$ alkyl, or
R$^1$ and R$^2$ taken together with the interposed nitrogen forms a heterocyclic group of the formula:

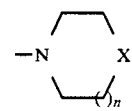

where n is one of the integers 0, 1 or 2;
X is —S— or

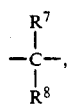

and

R[7] is H, hydroxy, $C_1-C_6$ alkyl, phenyl or phenyl substituted by $C_1-C_6$ alkyl, $C_1-C_6$ haloalkyl, halo, nitro, cyano or trifluoromethyl;

R[8] is H or $C_1-C_6$ alkyl; and

R[3], R[4], R[5] and R[6] are H, $C_1-C_6$ alkyl, $C_1-C_6$ alkoxy, halo, nitro, cyano, $C_1-C_6$ perhaloalkyl, $C_1-C_{16}$ alkoxycarbonyl or carboxyl.

In the above definitions, halo means fluorine, chlorine, bromine or iodine. The terms alkyl, alkenyl, alkanoyl, and alkoxy include both branched and straight chain hydrocarbon radicals where possible. The term $C_1-C_6$ perhaloalkyl refers to a $C_1-C_6$ alkyl group in which all hydrogens are replaced with halogen atoms, preferably fluorine. The term $C_2-C_{12}$ gemdialkyl refers, in this case, to a heterocyclic ring carbon as defined by NR[1]R[2] substituted by two alkyl groups having from 1 to 6 carbon atoms each.

DETAILED DESCRIPTION OF THE INVENTION

The Formula I compounds of this invention are prepared from an appropriately substituted 4-hydroxy-1-piperidinecarboxylic acid 4-phenoxyphenyl ester of Formula II. The preparation of this intermediate is given in Example 1 where a 4-phenoxyphenol, prepared by standard procedures, is reacted with trichloromethylchloroformate ("diphosgene") to give the corresponding 4-phenoxyphenylchloroformate which upon reaction with 4-hydroxypiperidine yields the intermediate carbamate shown below as Formula II:

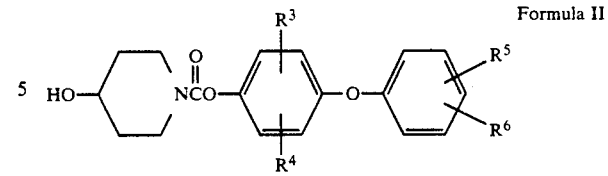

The Formula I compounds are synthesized from Formula II intermediates according to the following general reaction schemes. More detailed procedures are given in the specific procedures of Examples 1-19.

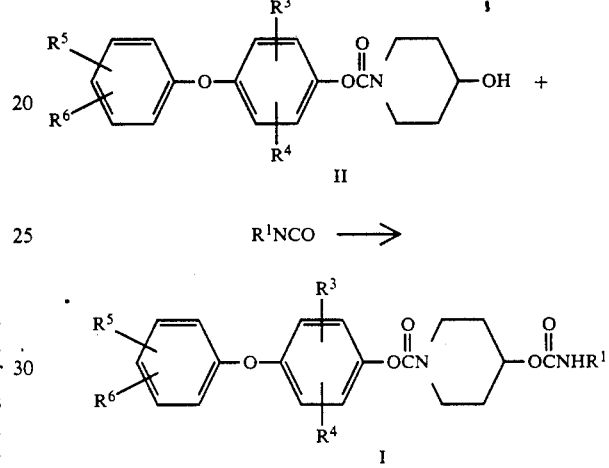

According to this procedure a Formula II intermediate is reacted with an alkyl or aryl isocyanate, either commerically available or prepared according to standard literature procedures, in a dry aprotic solvent such as methylene chloride, chloroform, benzene, toluene, acetonitrile or tetrahydrofuran. A catalyst, such as triethylamine, can be added to promote the reaction. The procedure of Example 2 is illustrative of Scheme A.

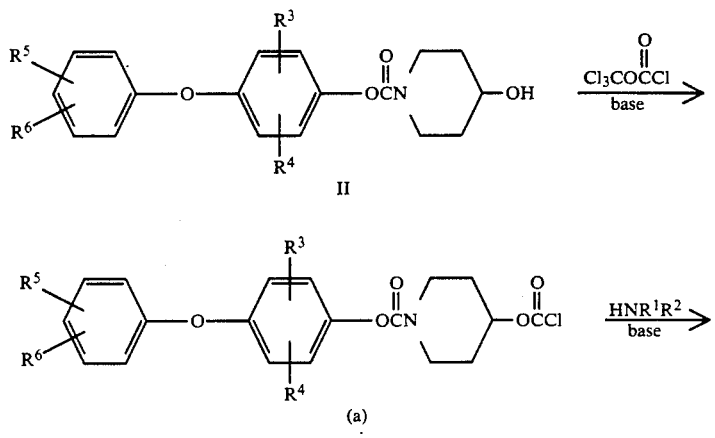

-continued
Scheme B.
Reaction of Chloroformate Ester of Formula II Intermediate With an Amine

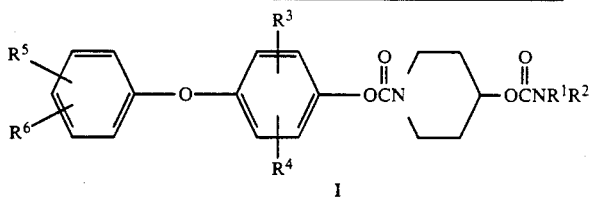

According to Scheme B, a Formula II intermediate is reacted with trichloromethylchloroformate in a dry aprotic solvent such as benzene, toluene, methylene chloride, acetonitrile or tetrahydrofuran in the presence of a base such as dimethylaniline or pyridine to form the intermediate chloroformate (a) in situ to which a primary or secondary amine is added to give the Formula I compound. This procedure is given in detail in Example 8.

Scheme C.
Reaction of A 4-Phenoxyphenylchloroformate With An Appropriately Substituted 4-Hydroxypiperidine Carbamate Ester.

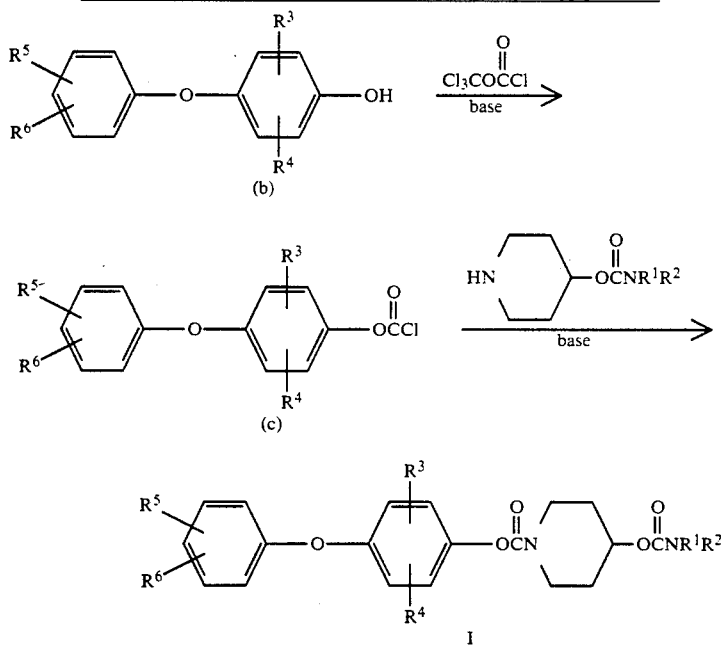

The 4-phenoxyphenylchloroformate (c) is prepared from the corresponding phenol (b) either by the procedure given in Example 1 (dry aprotic solvent, organic base) or by the aqueous base/immiscible organic solvent procedure (Schotten-Bauman procedure) shown in Example 18. The 4-phenoxyphenylchloroformate (c) is then reacted under anhydrous conditions with an appropriately substituted carbamic acid 4-piperidine ester, prepared separately, to obtain the Formula I compound. Examples 18 and 19 describe the procedures outlined in Scheme C in greater detail.

The following specific Examples 1–19 illustrate the synthesis of the Formula II intermediate and the procedures outlined in Schemes A, B and C. These specific examples are included for illustrative purposes only and are not to be construed as limiting to the scope of this disclosure in any way. Those skilled in the art may be aware of other procedures or modifications to prepare Formula I compounds. All starting materials or reagents are either commercially available or readily prepared by methods found in the literature.

EXAMPLE 1

4-Hydroxy-1-piperidinecarboxylic acid 4-phenoxyphenyl ester

A solution of 4-phenoxyphenol (30 g, 0.16 mol) and dimethylaniline (20.4 mL, 0.16 mol) in 200 mL of benzene plus 9 mL of dioxane was added dropwise over 1.5 hours under a nitrogen atmosphere to a solution of trichloromethyl chloroformate (9.7 mL, 0.08 mol) in 60 mL of benzene at ice bath temperature. After the addition, the cooling bath was removed and the stirring continued for 24 hours. The reaction mixture was filtered and the filtrate was then added dropwise under a nitrogen atmosphere to a solution of 4-hydroxypiperidine (16.3 g, 0.16 mol) and pyridine (26.1 mL, 0.32 mol) in 150 mL each of benzene, methylene chloride and tetrahydrofuran (THF) at ice bath temperature. After the addition, the reaction was stirred at ice bath temperature for 3 hours. The cooling bath was removed and the stirring continued overnight. The reaction mixture was diluted with benzene and washed with 1N HCl. The organic solution was separated, dried over anhydrous MgSO₄ and the solvent removed under reduced pressure to give 46.4 g of a yellow mushy solid. Purification by high pressure liquid chromatography (HPLC) with hexane: EtOAc mixtures gave 13.3 g of a white solid. Recrystallization from diisopropyl ether-methanol gave the title compound as a white crystalline solid (10.4 g, 21%), mp 128°–130° C.

Analysis: Calc'd for $C_{18}H_{19}NO_4$: C, 69.00; H, 6.11; N, 4.47. Found: C, 68.99; H, 6.06; N, 4.43.

EXAMPLE 2

4-[[(Butylamino)carbonyl]oxy]-1-piperidinecarboxylic acid 4-phenoxyphenyl ester

Triethylamine (360 μL, 2.6 mmol) was added dropwise under a nitrogen atmosphere to a solution of the alcohol produced in Example 1 (1.0 g, 3.2 mmol) and n-butyl isocyanate (430 μL, 3.8 mmol) in 15 mL of methylene chloride. After the addition, the solution was stirred at room temperature. When the reaction was complete as determined by thin layer chromatography (TLC), the solution was extracted with 1N HCl, dried (MgSO$_4$) and the solvent removed under reduced pressure to give 1.55 g of a white solid. Recrystallization from diisopropyl ether gave the title compound as a white crystalline solid (1.09 g, 85%), mp 77°–80° C.

Analysis: Calc'd for $C_{23}H_{28}N_2O_5$: C, 66.97; H, 6.84; N, 6.79. Found: C, 67.06; H, 7.13; N, 6.82.

EXAMPLE 3

4-[[(Hexylamino)carbonyl]oxy]-1-piperidinecarboxylic acid 4-phenoxyphenyl ester

In the same manner as described in Example 2 and substituting n-hexyl isocyanate for n-butyl isocyanate, the title compound was produced as a white crystalline solid after recrystallization of the crude reaction product from diisopropyl ether (1.12 g, 79%), mp 77°–82° C.

Analysis: Calc'd for $C_{25}H_{32}N_2O_5$: C, 68.16; H, 7.32; N, 6.36. Found: C, 68.28; H, 7.31; N, 6.41.

EXAMPLE 4

4-[[(Octylamino)carbonyl]oxy]-1-piperidinecarboxylic acid 4-phenoxyphenyl ester

In the same manner as described in Example 2 and substituting n-octyl isocyanate for n-butyl isocyanate, the title compound was produced as a white crystalline solid after recrystallization of the crude reaction product from diisopropyl ether (1.05 g, 70%), mp 73°–75° C.

Analysis: Calc'd for $C_{27}H_{36}N_2O_5$: C, 69.21; H, 7.74; N, 5.98. Found: C, 69.22; H, 7.79; N, 6.26.

EXAMPLE 5

4-[[(Cyclohexylamino)carbonyl]oxy]-1-piperidinecarboxylic acid 4-phenoxyphenyl ester In the same manner as described in Example 2 and substituting cyclohexyl isocyanate for n-butyl isocyanate, the title compound was produced as a white crystalline solid after recrystallization of the crude reaction product from diisopropyl ether (855 mg, 61%), mp 137°–139° C.

Analysis Calc'd for $C_{25}H_{30}N_2O_5$: C, 68.47; H, 6.90; N, 6.39. Found: C, 68.59; H, 7.00; N, 6.42.

EXAMPLE 6

4-[[(Dodecylamino)carbonyl]oxy]-1-piperidinecarboxylic acid 4-phenoxyphenyl ester In the same manner as described in Example 2 and substituting dodecyl isocyanate for n-butyl isocyanate, the title compound was produced as a white crystalline solid (989 mg, 58%) after purification of the crude reaction product by chromatography on silica gel (3% ethyl acetate-methylene chloride), mp 65°–67° C.

Analysis Calc'd for $C_{31}H_{44}N_2O_5$: C, 70.96; H, 8.45; N, 5.34. Found: C, 71.08; H, 8.52; N, 5.32.

EXAMPLE 7

4-[[(Octadecylamino)carbonyl]oxy]-1-piperidinecarboxylic acid 4-phenoxyphenyl ester Triethylamine (0.9 mL, 6.4 mmol) was added under a nitrogen atmosphere to a solution of the alcohol produced in Example 1 (2.5 g, 8.0 mmol) and octadecyl isocyanate (3.3 mL, 9.6 mmol) in 50 mL of chloroform. After the addition the solution was refluxed. Additional quantities of the isocyanate were added as necessary to drive the reaction to completion. The reaction was monitored by TLC. In this reaction a total of 3.2 equivalents of octadecyl isocyanate were used. The total reflux time was 76 hrs. At the end of the reaction the solution was extracted with 1N HCl, dried (MgSO$_4$) and the solvent removed under reduced pressure to give 9.04 g of a light brown solid. Recrystallization from diisopropyl ether-hexane gave the title compound as an off-white crystalline solid (3.19 g, 65%), mp 75°–78° C.

Analysis: Calc'd for $C_{37}H_{56}N_2O_5$: C, 72.99; H, 9.27; N, 4.60. Found: C, 72.87; H, 8.94; N, 4.57.

EXAMPLE 8

4-[[[(1,5-Dimethylhexyl)amino]carbonyl]oxy]-1-piperidinecarboxylic acid 4-phenoxyphenyl ester A solution of the alcohol produced in Example 1 (2.0 g, 6.38 mmol) and dimethylaniline (810 μL, 6.38 mmol) in 20 mL of benzene plus 1 mL of dioxane was added dropwise under a nitrogen atmosphere to a solution of trichloromethyl chloroformate (380 μL, 3.19 mmol) in 5 mL of benzene at ice bath temperature. After the addition, the cooling bath was removed and the stirring continued for 24 hours. The reaction was cooled to ice bath temperature and a solution of 1,5-dimethylhexylamine (1.1 mL, 6.38 mmol) and pyridine (1.0 mL, 12.8 mmol) in 10 mL of benzene was added dropwise. After the addition, the reaction was stirred at ice bath temperature for 2 hours. The cooling bath was removed and the reaction stirred overnight. The reaction was diluted with benzene and extracted two times with 1N HCl. The organic solution was dried (MgSO$_4$) and the solvent was removed under reduced pressure to give 2.88 g of an oil. Purification by column chromatography on 300 g of silica gel (230–400 mesh) using methylene chloride as an eluent gave 1.18 g of a waxy yellow solid. Recrystallization from hexane gave the title compound as a light yellow crystalline solid (879 mg, 29%), mp 59°–61° C.

Analysis: Calc'd for $C_{27}H_{36}N_2O_5$: C, 69.21; H, 7.74; N, 5.98. Found: C, 68.91; H, 7.75; N, 5.81.

EXAMPLE 9

4-[[(4-Methyl-1-piperidinyl)carbonyl]oxy-1-piperidinecarboxylic acid 4-phenoxyphenyl ester In the same manner as described in Example 8 and substituting 4-methylpiperidine for 1,5-dimethylhexylamine, the title compound was produced as a white crystalline solid (1.65 g, 59%) after purification of the crude reaction product by chromatography on silica gel (methylene chloride) and recrystallization from methylene chloride-hexane, mp 116°–118° C.

Analysis: Calc'd for $C_{25}H_{30}N_2O_5$: C, 68.47; H, 6.90; N, 6.39. Found: C, 68.43; H, 7.05; N, 6.78.

EXAMPLE 10

4-[[[[[4-(2,2-Dimethylpropyl)phenyl]methyl]heptylamino]carbonyl]oxy]-1-piperidinecarboxylic acid 4-phenoxyphenyl ester In the same manner as described in Example 8 and substituting [[4-(2,2-dimethylpropyl)phenyl]methyl]heptylamine for 1,5-dimethylhexylamine, the title compound was produced as a white crystalline solid (1.63 g, 42%) after purification of the crude reaction product by chromatography on silica gel (hexane-ethyl acetate) and recrystallization from diisopropyl ether, mp 91°–92° C.

Analysis: Calc'd for $C_{38}H_{50}N_2O_5$: C, 74.24; H, 8.20; N, 4.56. Found: C, 74.31; H, 7.87; N, 4.65.

EXAMPLE 11

4-[[(Methylamino)carbonyl]oxy]-1-piperidinecarboxylic acid 4-phenoxyphenyl ester In the same manner as described in Example 7 and substituting methyl isocyanate for octadecyl isocyanate, except that the reaction was stirred at 40° C. for five days and room temperature for two days, the title compound was produced as a white crystalline solid after recrystallization of the crude reaction product from diisopropyl ether (626 mg, 26%), mp 117°–119° C.

Analysis: Calc'd for $C_{20}H_{22}N_2O_5$: C, 64.85; H, 5.99; N, 7.56. Found: C, 64.67; H, 6.09; N, 7.64.

EXAMPLE 12

4-[[(Diethylamino)carbonyl]oxy]-1-piperidinecarboxylic acid 4-phenoxyphenyl ester In the same manner as described in Example 8 and substituting diethylamine for 1,5-dimethylhexylamine, the title compound was produced as a white crystalline solid (940 mg, 36%) after purification of the crude reaction product by chromatography on silica gel (hexane-ethyl acetate) and recrystallization from diisopropyl ether, mp 79°–81° C.

Analysis: Calc'd for $C_{23}H_{28}N_2O_5$: C, 66.97; H, 6.84; N, 6.79. Found: C, 67.30; H, 6.82; N, 6.74.

EXAMPLE 13

4-[[[(4-Phenylbutyl)amino]carbonyl]oxy]-1-piperidinecarboxylic acid 4-phenoxyphenyl ester In the same manner as described in Example 8 and substituting 4-phenylbutylamine for 1,5-dimethylhexylamine, the title compound was produced as a crystalline solid (1.33 g, 43%) after recrystallization of the crude reaction product from diisopropyl ether, mp 129°–131° C.

Analysis: Calc'd for $C_{29}H_{32}N_2O_5$: C, 71.29; H, 6.60; N, 5.73. Found: C, 70.99; H, 6.57; N, 5.59.

EXAMPLE 14

4-[[(Z)-9-Octadecenylamino)carbonyl]oxy]-1-piperidinecarboxylic acid 4-phenoxyphenyl ester In the same manner as described in Example 8 and substituting (Z)-9-octadecenylamine for 1,5-dimethylhexylamine, the title compound was produced as a white waxy solid (2.69 g, 70%) after purification by HPLC and recrystallization from hexane, mp 58°–60° C.

Analysis: Calc'd for $C_{37}H_{54}N_2O_5$: C, 73.23; H, 8.97; N, 4.62. Found: C, 73.27; H, 8.75; N, 4.69.

EXAMPLE 15

4-Thiomorpholinecarboxylic acid 1-[(4-phenxoyphenoxy)carbonyl]-4-piperidinyl ester In the same manner as described in Example 8 and substituting thiomorpholine for 1,5-dimethylhexylamine, the title compound was produced as a white crystalline solid (1.22 g, 43%) after purification by HPLC and recrystallization from diisopropyl ether, mp 108°–110° C.

Analysis: Calc'd for $C_{23}H_{26}N_2O_5S$: C, 62.43; H, 5.92; N, 6.33. Found: C, 62.37; H, 5.87; N, 6.29.

EXAMPLE 16

4-Phenyl-1-piperidinecarboxylic acid 1-[(4-phenoxyphenoxy)carbonyl]-4-piperidinyl ester In the same manner as described in Example 8 and substituting 4-phenylpiperidine for 1,5-dimethylhexylamine, the title compound was produced as a white crystalline solid (913 mg, 29%) after crystallization of the product from hexane-ethyl acetate and recrystallization from diisopropyl ether, mp 125°–126° C.

Analysis: Calc'd for $C_{30}H_{32}N_2O_5$: C, 71.98; H, 6.44; N, 5.60. Found: C, 71.69; H, 6.76; N, 5.60.

EXAMPLE 17

4-[[[(Cyclohexylmethyl)amino]carbonyl]oxy]-1-piperidinecarboxylic acid 4-phenoxyphenyl ester In the same manner as described in Example 8 and substituting aminomethylcyclohexane for 1,5-dimethylhexylamine, the title compound was produced as a white crystalline solid (1.15 g, 40%) after purification by HPLC and recrystallization from diisopropyl ether, mp 103°–105° C.

Analysis: Calc'd for $C_{26}H_{32}N_2O_5$: C, 69.01; H, 7.13; N, 6.19. Found: C, 69.02; H, 7.19; N, 6.37.

EXAMPLE 18

4-[[(Hexylamino)carbonyl]oxy]-1-piperidinecarboxylic acid 4-(4-methylphenoxy)phenyl ester A mixture of p-cresol (41.89 mL, 0.4 mol) and sodium methoxide (21.2 g, 0.4 mol) in 400 mL of anhydrous pyridine was refluxed with stirring under nitrogen for 1 hour. The methanol was distilled off. After cooling to room temperature 4-bromoanisole (49.1 mL, 0.4 mol) and copper (I) chloride (6 g, 0.06 mol) were added and the mixture refluxed for 17 hours. Most of the pyridine was removed by distillation. The residue was poured into water, acidified with dilute HCl (1:1 conc. HCl:H$_2$O) and extracted with methylene chloride. The organic layer was extracted two times with 1N NaOH, dried (MgSO$_4$) and the solvent removed under reduced pressure to give a brown solid. Purification by HPLC (hexane-methylene chloride) gave 4-methoxy-4'-methyldiphenyl ether as a light tan crystalline solid (73.47 g, 88%), mp 39°–44° C.

Analysis: Calc'd for $C_{14}H_{14}O_2$: C, 78.48; H, 6.59. Found: C, 78.22; H, 6.67.

4-Methoxy-4'-methyldiphenyl ether (25 g, 0.12 mol) was dissolved in 120 mL of glacial acetic acid and then treated with 100 mL of 48% HBr. The mixture was heated to reflux during which time everything dissolved. The resulting solution was refluxed for 4.5 hours. The reaction mixture was poured into ice water and extracted three times with methylene chloride. The combined organic extracts were washed five times with water, dried (MgSO4) and the solvent removed under reduced pressure to give a brown solid. Purification by HPLC (hexane-methylene chloride) gave 4-hydroxy-4'-methyldiphenyl ether as an off-white solid (19.50 g, 83%), mp 74°–76° C.

Analysis: Calc'd for $C_{13}H_{12}O_2$: C, 77.98; H, 6.04. Found: C, 78.31; H, 6.13.

A solution of 4-hydroxy-4'-methyldiphenyl ether (2.0 g, 10 mmol) in 10 mL of 1N NaOH was added dropwise over 1.5 hours under a nitrogen atmosphere to a solution of trichloromethyl chloroformate (1.2 mL, 10 mmol) in 20 mL of chloroform at ice bath temperature. After the addition the reaction was stirred at ice bath temperature for 1.5 hours. The reaction was washed with water. The organic solution was dried (MgSO4) and the solvent removed under reduced pressure to give the chloroformate as a yellow oil (2.4 g), MS m/e 262 (M+).

A solution of the chloroformate (439 mg, 1.67 mmol), prepared in the preceding paragraph, in 10 mL of methylene chloride was added dropwise over 30 minutes under a nitrogen atmosphere to a solution of hexylcarbamic acid 4-piperidinyl ester (379 mg, 1.66 mmol) and triethylamine (231 μL, 1.66 mmol) in 10 mL of methylene chloride at ice bath temperature. After the addition the reaction was stirred at ice bath temperature for 1 hour. The cooling bath was removed and the stirring continued for 3.5 hours. The reaction was extracted with 1N HCl, dried (MgSO4) and the solvent removed under reduced pressure to give 712 mg of a light yellow solid. Purification of the solid by chromatography on 350 g of silica gel (230–400 mesh) using 2% ethyl acetatemethylene chloride as an eluent gave the title compound as a white crystalline solid, mp 84°–85° C.

Analysis: Calc'd for $C_{26}H_{34}N_2O_5$: C, 68.70; H, 7.54; N, 6.16. Found: C, 68.70; H, 7.66; N, 6.15.

EXAMPLE 19

4-[[(Hexylamino)carbonyl]oxy]-1-piperidinecarboxylic acid 4-(4-methoxyphenoxy)phenyl ester In the same manner as described in paragraph 1 of Example 18, 4-benzyloxy-4'-methoxydiphenyl ether was produced as a white crystalline solid after trituration with hexane of the HPLC (eluent: hexane-methylene chloride) purified material (24.53 g, 64%), mp 106°–108° C.

Analysis: Calc'd for $C_{20}H_{18}O_3$: C, 78.41; H, 5.92. Found: C, 78.29; H, 5.90.

4-Benzyloxy-4'-methoxydiphenyl ether was dissolved in 150 mL of ethyl acetate. To this solution, 2 g of 10% Pd-C was added and the mixture hydrogenated at room temperature and 25 psi for 24 hours. After removal of the catalyst by filtration through Celite and removal of the solvent under reduced pressure, 5.63 g of a crystalline solid remained. Recrystallization of this material from diisopropyl ether-hexane produced 4-hydroxy-4'-methoxydiphenyl ether as a white crystalline solid (4.74 g, 84%), mp 88°–90° C.

Analysis: Calc'd for $C_{13}H_{12}O_3$: C, 72.21; H, 5.59. Found: C, 72.12; H, 5.29.

A solution of 4-hydroxy-4'-methoxydiphenyl ether (2.0 g, 9.25 mmol) and dimethylaniline (1.2 mL, 9.46 mmol) in 20 mL of benzene plus 1 mL of dioxane was added dropwise under a nitrogen atmosphere to a solution of trichloromethyl chloroformate (0.56 mL, 4.64 mmol) in 10 mL of benzene at ice bath temperature. After the addition the reaction was stirred at ice bath temperature for 1.5 hours. The cooling bath was removed and the stirring continued for 19 hours. The reaction was cooled to ice bath temperature and a solution of hexylcarbamic acid 4-piperidinyl ester (2.1 g, 9.20 mmol) and pyridine (1.5 mL, 18.5 mmol) in 20 mL of benzene was added dropwise. After the addition the reaction was stirred at ice bath temperature for 2.5 hours. The cooling bath was removed and the reaction stirred overnight. The reaction was extracted two times with 1N HCl, dried (MgSO4) and the solvent removed under reduced pressure to give 3.55 g of a light yellow crystalline solid. Purification of this solid by chromatography on 400 g of silica gel (230–400 mesh) using ethyl acetate-methylene chloride as an eluent gave the title compound as a white crystalline solid, mp 91°–93° C.

Analysis: Calc'd for $C_{26}H_{34}N_2O_6$: C, 66.36; H, 7.28; N, 5.95. Found: C, 66.42; H, 7.27; N, 5.95.

EXAMPLE 20

4-[[(Hexylamino)carbonyl]oxy]-1-piperidinecarboxylic acid 2-fluoro-4-phenoxyphenyl ester A solution of 85% potassium hydroxide (3.88 g, 58.8 mmol) in 3 ml of water was added to a solution of phenol (6.1 g, 64.8 mmol) in 40 ml of toluene. The resulting mixture was refluxed under a nitrogen atmosphere and a Dean-Stark trap for 3.5 hours. After standing overnight at room temperature, the toluene was removed by distillation under reduced pressure and the resulting solid dried under high vacuum. To this solid, 4-bromo-2-fluoroanisole (6.4 ml, 49.6 mmol) and copper (1) chloride (0.1 g, 1.0 mmol) were added and the mixture heated at 180° C. for 2 hours. After cooling to room temperature, the mixture was partitioned between diethyl ether and water and extracted. The ether layer was extracted two times with 1N NaOH, dried (MgSO4) and the solvent was removed under reduced pressure to give 9.73 g of a brown oil. Purification of the material by column chromatography (silica gel, 230–400 mesh) using hexane-methylene chloride as the eluent gave 3-fluoro-4-methoxydiphenyl ether as a clear oil (8.56 g, 79%): IR(film) 3080, 3020, 2970, 2940, 2850, 1595, 1510 and 1490 cm$^{-1}$; ms m/e, 218 (m+).

In the same manner as described in the second paragraph of Example 18, 3-fluoro-4-hydroxydiphenyl ether was produced as an oil (6.57 g, 92%): ms m/e, 204 (m+).

Analysis: Calc'd for $C_{12}H_9FO_2$: C, 70.58; H, 4.44. Found: C, 70.24; H, 4.33.

Following the procedure of Example 18, paragraph 3 and substituting 3-fluoro-4-hydroxydiphenyl ether for 4-hydroxy-4'-methyldiphenyl ether, the title compound is obtained.

EXAMPLE 21

4-[[(Hexylamino)carbonyl]oxy]-1-piperidinecarboxylic acid 2-bromo-4-phenoxyphenyl ester Bromine (21.0 g, 0.13 mol) was added dropwise under a nitrogen atmosphere over 3 hours to an ice cold solution of 4-phenoxyphenol (25.0 g, 0.13 mol) in 125 ml of carbon disulfide. After the addition, the reaction was stirred at ice bath temperature for 1 hour. The cooling bath was removed and the stirring continued at room temperature overnight. The solvent was removed under reduced pressure. The residual oil was taken up in methylene chloride and the organic solution was washed with brine, dried (MgSO$_4$) and the solvent was removed under reduced pressure to give 37.2 g of a light brown oil. Purification of this material on HPLC using methylene chloride as an eluent gave 2-bromo-4-phenoxyphenol as a light yellow oil (29.7 g, 85%): IR (film) 3500, 3050, 3020, 1580 and 1470 cm$^{-1}$; ms m/e, 264/266 (m+).

Following the procedure of Example 18, paragraph 3 and substituting 3-bromo-4-hydroxydiphenyl ether for 4-hydroxy-4'-methyldiphenyl ether, the title compound is obtained.

In-Vitro and In-Vivo Pharmacological Procedures

1. The ability of the compounds of this invention to inhibit acyl-coenzyme A: cholesterol acyltransferase was established by initially showing that they inhibited intracellular cholesterol esterification by subjecting them to the standard experimental test procedure of Ross et al., J. Biol. Chem. 259, 815 (1984). The results are reported in the following table, where available, in terms of the percent inhibition at 25 μM and the IC$_{50}$ (μM).

2. The ability of the compounds of this invention to inhibit the formation of cholesteryl esters and thereby interfere with and prevent assimilation of cholesterol into the lymphatic system and ultimately the blood stream was established by incubating the compounds at 37° C. with a mixture of cholesterol and oleic acid in the presence of buffered cholesterol esterase [(EC 3.1.1.13) Sigma Company, St. Louis, Mo., U.S.A., No. C-1892, from bovine pancreas] and measuring the amount of ester formed, according to the procedure of Field, J. of Lipid Research, 25 389 (1984). The concentration of test compound that inhibits one-half of the ester formation (IC$_{50}$, μM) is given in the following table.

The in vivo cholesterol absorption studies were conducted in normal rats by oral administration of the compound being tested in propylene glycol and olive oil followed by oral administration of [4-$^{14}$C] cholesterol in propylene glycol and olive oil, otherwise following the procedure of Cayen et al., J. Lipid Res. 20 162 (1979). The serum radioactivity was measured at six hours after dosing. The results of this study are reported in the following table, where available, as percent decrease compared to control and in terms of the effective dose (ED$_{50}$) inhibiting fifty-percent of the absorption of the control animals.

TABLE I

| Example | In Vitro Results % inhibition at 25 μM/IC$_{50}$ (μM) | | In Vivo Results Effect on Absorption of $^{14}$C-Chol.-6 hr-normal rat % Decrease (mg/kg) |
|---|---|---|---|
| | ACAT | CEH | |
| 2 | 96%/2 | 2.3 | N.D. |
| 3 | 94%/0.64 | 9.8 | 85%(10) |
| 4 | 94%/0.82 | >100 | 92%(100) |
| 5 | 92%/1.68 | 9.5 | 89%(10) |
| 6 | 88%/0.51 | 16 | 57%(10) |
| 7 | N.D. | >100 | 28%(25) |
| 8 | N.D. | 13 | N.D. |
| 9 | N.D. | 1.1 | N.D. |
| 10 | 84%/3.30 | >100 | N.D. |
| 11 | N.D. | 2.1 | N.D. |
| 12 | 93%/1.37 | 11.4 | N.D. |
| 13 | 96%/0.23 | 5 | 41%(10) |
| 14 | N.D. | 43 | 21%(25) |
| 15 | N.D. | 79 | N.D. |
| 16 | 91%/0.51 | 12 | 48%(10) |
| 17 | 97%/0.49 | 19 | 68%(3) |
| 18 | N.D. | 2 | 25%(10) |

TABLE I-continued

| Example | In Vitro Results % inhibition at 25 μM/IC$_{50}$ (μM) | | In Vivo Results Effect on Absorption of $^{14}$C-Chol.-6 hr-normal rat % Decrease (mg/kg) |
|---|---|---|---|
| | ACAT | CEH | |
| 19 | N.D. | 2.8 | 29%(10) |

Thus, the compounds of this invention are useful in the treatment of high serum cholesterol levels and associated disease states such as coronary heart disease, atherosclerosis, familial hypercholesterolemia, hyperlipemia and similar disease states. As such, they may be administered to a hypercholesterolemic patient, orally or parenterally, in an amount sufficient to reduce serum cholesterol concentrations to the desired level. The dosage regimen for therapeutic use of the anti-hypercholesterolemic agents of this invention will vary with the route of administration, size and age of the person under treatment, as well as the severity of the dysfunction under treatment. Therefore, the treatment must be individualized for the patient under guidance of the attending physician.

The compounds of this invention may be administered by conventional oral or parenteral routes as solids, liquids or isotonic solutions. Conventional adjuvants known to the art may be combined with the compounds to provide compositions and solutions for administration purposes, although it is considered desirable and feasible to use the compounds neat or pure without additives other than for the purpose of providing suitable pharmaceutically acceptable solid or liquid dosage units.

What is claimed is:

1. A compound of the formula:

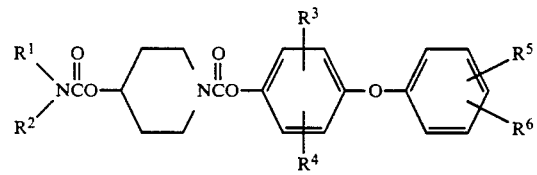

in which
R$^1$ is H, C$_1$–C$_{20}$ alkyl, C$_3$–C$_{20}$ alkenyl, C$_3$–C$_8$ cycloalkyl, cycloalkylalkyl where the cycloalkyl moiety has from 3 to 8 carbon atoms and the alkyl moiety has from 1 to 6 carbon atoms, phenyl, phenyl substituted by C$_1$–C$_6$ alkyl, C$_1$–C$_6$ alkoxy, halo, nitro, cyano or trifluoromethyl; phenylalkyl where the alkyl moiety has from 1 to 20 carbons, or phenylalkyl where the phenyl group is substituted by C$_1$–C$_6$ alkyl, C$_1$–C$_6$ alkoxy, halo, nitro, cyano, trifluoromethyl or phenyl; R$^2$ is H or C$_1$–C$_6$ alkyl; or R$^1$ and R$^2$ taken together with the interposed nitrogen forms a heterocyclic group of the formula:

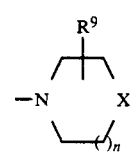

where n is one of the intergers 0, 1 or 2;
X is —O—, —S—, or

and $R^7$ is H, hydroxy, $C_1$-$C_6$ alkyl, $C_2$-$C_6$ alkanoyloxy, $C_1$-$C_6$ hydroxyalkyl, carboxyl, $C_1$-$C_{16}$ alkoxycarbonyl, phenyl or phenyl substituted with $C_1$-$C_6$ alkyl, $C_1$-$C_6$ haloalkyl, $C_1$-$C_6$ perhaloalkyl, halo, nitro or cyano;

$R^8$ is H or $C_1$-$C_6$ alkyl or $R^7$ and $R^8$ taken together with the intervening carbon atom forms a polymethylene ring of 3 to 7 carbon atoms;

$R^9$ is H, $C_1$-$C_6$ alkyl or $C_2$-$C_{12}$ gemdialkyl; and $R^3$, $R^4$, $R^5$ and $R^6$ are H, $C_1$-$C_6$ alkyl, $C_1$-$C_6$ alkoxy, halo, nitro, cyano, $C_1$-$C_6$ perhaloalkyl, $C_1$-$C_{16}$ alkoxycarbonyl, or carboxyl.

2. A compound of the formula:

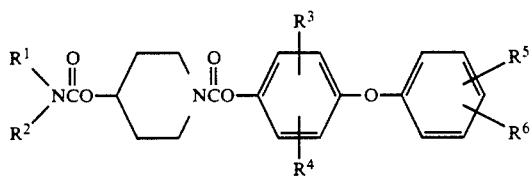

in which $R^1$ is $C_1$-$C_{20}$ alkyl, $C_3$-$C_{20}$ alkenyl, $C_3$-$C_8$ cycloalkyl, cycloalkylalkyl in which the cycloalkyl moiety has from 3 to 8 carbon atoms and the alkyl moiety has from 1 to 6 carbon atoms, phenylalkyl where the alkyl moiety has from 1 to 20 carbon atoms, and substituted phenylalkyl where the phenyl group is substituted by $C_1$-$C_6$ alkyl, $C_1$-$C_6$ alkoxy, halo, nitro, cyano, trifluoromethyl, or phenyl;

$R^2$ is H or $C_1$-$C_6$ alkyl, or $R^1$ and $R^2$ taken together with the interposed nitrogen forms a heterocyclic group of the formula:

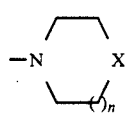

where n is one of the integers 0, 1 or 2;

X is —S— or

and $R^7$ is H, hydroxy, $C_1$-$C_6$ alkyl, phenyl or phenyl substituted by $C_1$-$C_6$ alkyl, $C_1$-$C_6$ haloalkyl, halo, nitro, cyano or trifluoromethyl;

$R^8$ is H or $C_1$-$C_6$ alkyl; and $R^3$, $R^4$, $R^5$ and $R^6$ are H, $C_1$-$C_6$ alkyl, $C_1$-$C_6$ alkoxy, halo, nitro, cyano, $C_1$-$C_6$ perhaloalkyl, $C_1$-$C_{16}$ alkoxycarbonyl or carboxyl.

3. A compound according to claim 1 which is 4-[[(butylamino)carbonyl]oxy]-1-piperidinecarboxylic acid 4-phenoxyphenyl ester.

4. A compound according to claim 1 which is 4-[[(hexylamino)carbonyl]oxy]-1-piperidinecarboxylic acid 4-phenoxyphenyl ester.

5. A compound according to claim 1 which is 4-[[(octylamino)carbonyl]oxy]-1-piperidinecarboxylic acid 4-phenoxyphenyl ester.

6. A compound according to claim 1 which is 4-[[(cyclohexylamino)carbonyl]oxy]-1-piperidinecarboxylic acid 4-phenoxyphenyl ester.

7. A compound according to claim 1 which is 4-[[(dodecylamino)carbonyl]oxy]-1-piperidinecarboxylic acid 4-phenoxyphenyl ester.

8. A compound according to claim 1 which is 4-[[(octadecylamino)carbonyl]oxy]-1-piperidinecarboxylic acid 4-phenoxyphenyl ester.

9. A compound according to claim 1 which is 4-[[[(1,5-dimethylhexyl)amino]-carbonyl]oxy]-1-piperidinecarboxylic acid 4-phenoxyphenyl ester.

10. A compound according to claim 1 which is 4-[[(4-methyl-1-piperidinyl)carbonyl]oxy]-1-piperidinecarboxylic acid 4-phenoxyphenyl ester.

11. A compound according to claim 1 which is 4-[[[[4-(2,2-dimethylpropyl)phenyl]-methyl]heptylamino]carbonyl]oxy]-1-piperidinecarboxylic acid 4-phenoxyphenyl ester.

12. A compound according to claim 1 which is 4-[[(methylamino)carbonyl]oxy]-1-piperidinecarboxylic acid 4-phenoxyphenyl ester.

13. A compound according to claim 1 which is 4-[[(diethylamino)carbonyl]oxy]-1-piperidinecarboxylic acid 4-phenoxyphenyl ester.

14. A compound according to claim 1 which is 4-[[[(4-phenylbutyl)amino]carbonyl]oxy]-1-piperidinecarboxylic acid 4-phenoxyphenyl ester.

15. A compound according to claim 1 which is 4-[[(Z)-9-octadecenylamino)carbonyl]oxy]-1-piperidinecarboxylic acid 4-phenoxyphenyl ester.

16. A compound according to claim 1 which is 4-thiomorpholinecarboxylic acid 1-[(4-phenoxyphenoxy)carbonyl]-4-piperidinyl ester.

17. A compound according to claim 1 which is 4-phenyl-1-piperidinecarboxylic acid 1-[(4-phenoxyphenoxy)carbonyl]-4-piperidinyl ester.

18. A compound according to claim 1 which is 4-[[[(cyclohexylmethyl)amino]carbonyl]oxy]-1-piperidinecarboxylic acid 4-phenoxyphenyl ester.

19. A compound according to claim 1 which is 4-[[(hexylamino)carbonyl]oxy]-1-piperidinecarboxylic acid 4-(4-methylphenoxy)phenyl ester.

20. A compound according to claim 1 which is 4-[[(hexylamino)carbonyl]oxy]-1-piperidinecarboxylic acid 4-(4-methoxyphenoxy)phenyl ester.

21. A process for reducing cholesterol absorption in a mammal in need of reduced serum cholesterol levels which comprises internally administering thereto a therapeutically effective amount for lowering serum cholesterol of a compound of the formula:

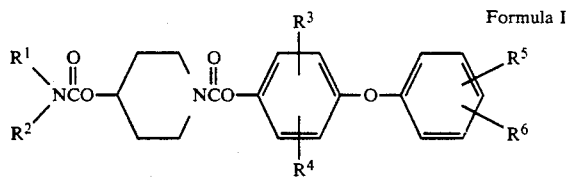

Formula I in which

R[1] is H, $C_1$-$C_{20}$ alkyl, $C_3$-$C_{20}$ alkenyl, $C_3$-$C_8$ cycloalkyl, cycloalkylalkyl where the cycloalkyl moiety has from 3 to 8 carbon atoms and the alkyl moiety has from 1 to 6 carbon atoms, phenyl, phenyl substituted by $C_1$-$C_6$ alkyl, $C_1$-$C_6$ alkoxy, halo, nitro, cyano or trifluoromethyl; phenylalkyl where the alkyl moiety has from 1 to 20 carbons, or phenylalkyl where the phenyl group is substituted by $C_1$-$C_6$ alkyl, $C_1$-$C_6$ alkoxy, halo, nitro, cyano, trifluoromethyl or phenyl; $R^2$ is H or $C_1$-$C_6$ alkyl; or $R^1$ and $R^2$ taken together with the interposed nitrogen forms a heterocyclic group of the formula:

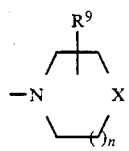

where n is one of the intergers 0, 1 or 2;
X is —O—, —S—, or

and $R^7$ is H, hydroxy, $C_1$-$C_6$ alkyl, $C_2$-$C_6$ alkanoyloxy, $C_1$-$C_6$ hydroxyalkyl, carboxyl, $C_1$-$C_{16}$ alkoxycarbonyl, phenyl or phenyl substituted with $C_1$-$C_6$ alkyl, $C_1$-$C_6$ haloalkyl, $C_1$-$C_6$ perhaloalkyl, halo, nitro or cyano;

$R^8$ is H or $C_1$-$C_6$ alkyl or $R^7$ and $R^8$ taken together with the intervening carbon atom forms a polymethylene ring of 3 to 7 carbon atoms;

$R^9$ is H, $C_1$-$C_6$ alkyl or $C_2$-$C_{12}$ gemdialkyl; and $R^3$, $R^4$, $R^5$ and $R^6$ are H, $C_1$-$C_6$ alkyl, $C_1$-$C_6$ alkoxy, halo, nitro, cyano, $C_1$-$C_6$ perhaloalkyl, $C_1$-$C_{16}$ alkoxycarbonyl, or carboxyl.

22. A parmaceutical composition for lowering serum cholesterol which comprises:

a. a therapeutically effective amount of a compound of the formula:

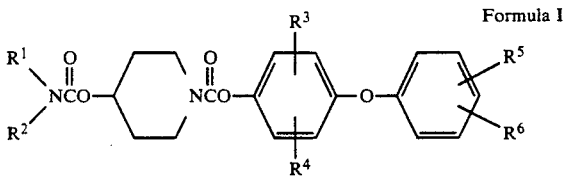

Formula I in which

R[1] is H, $C_1$-$C_{20}$ alkyl, $C_3$-$C_{20}$ alkenyl, $C_3$-$C_8$ cycloalkyl, cycloalkylalkyl where the cycloalkyl moiety has from 3 to 8 carbon atoms and the alkyl moiety has from 1 to 6 carbon atoms, phenyl, phenyl substituted by $C_1$-$C_6$ alkyl, $C_1$-$C_6$ alkoxy, halo, nitro, cyano or trifluoromethyl; phenylalkyl where the alkyl moiety has from 1 to 20 carbons, or phenylalkyl where the phenyl group is substituted by $C_1$-$C_6$ alkyl, $C_1$-$C_6$ alkoxy, halo, nitro, cyano, trifluoromethyl or phenyl; $R^2$ is H or $C_1$-$C_6$ alkyl; or $R^1$ and $R^2$ taken together with the interposed nitrogen forms a heterocyclic group of the formula:

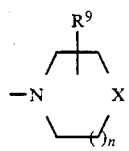

where n is one of the intergers 0, 1 or 2;
X is —O—, —S—, or

and $R^7$ is H, hydroxy, $C_1$-$C_6$ alkyl, $C_2$-$C_6$ alkanoyloxy, $C_1$-$C_6$ hydroxyalkyl, carboxyl, $C_1$-$C_{16}$ alkoxycarbonyl, phenyl or phenyl substituted with $C_1$-$C_6$ alkyl, $C_1$-$C_6$ haloalkyl, $C_1$-$C_6$ perhaloalkyl, halo, nitro or cyano;

$R^8$ is H or $C_1$-$C_6$ alkyl or $R^7$ and $R^8$ taken together with the intervening carbon atom forms a polymethylene ring of 3 to 7 carbon atoms;

$R^9$ is H, $C_1$-$C_6$ alkyl or $C_2$-$C_{12}$ gemdialkyl;

$R^3$, $R^4$, $R^5$ and $R^6$ are H, $C_1$-$C_6$ alkyl, $C_1$-$C_6$ alkoxy, halo, nitro, cyano, $C_1$-$C_6$ perhaloalkyl, $C_1$-$C_{16}$ alkoxycarbonyl, or carboxyl, and b. a pharmaceutical carrier.

* * * * *